(12) United States Patent
Conrady

(10) Patent No.: US 6,911,771 B1
(45) Date of Patent: Jun. 28, 2005

(54) FLUORESCENT FILM WITH LUMINESCENT PARTICLES

(75) Inventor: Jürgen Conrady, Berlin (DE)

(73) Assignee: PlasmaPhotonics GmbH, Berlin (DE)

( * ) Notice: Subject to any disclaimer, the term of this patent is extended or adjusted under 35 U.S.C. 154(b) by 16 days.

(21) Appl. No.: 10/069,039

(22) PCT Filed: Sep. 7, 2000

(86) PCT No.: PCT/DE00/03155
§ 371 (c)(1),
(2), (4) Date: Feb. 15, 2002

(87) PCT Pub. No.: WO01/21728
PCT Pub. Date: Mar. 29, 2001

(30) Foreign Application Priority Data

Sep. 20, 1999 (DE) .......................................... 199 46 125

(51) Int. Cl.$^7$ .......................... C09K 11/02; H01J 61/46; F21K 2/00
(52) U.S. Cl. .................. 313/485; 313/502; 252/301.16; 428/447
(58) Field of Search ................................ 313/483–489, 313/112, 635; 428/447, 917; 427/67, 226; 252/301.4 F, 301.16

(56) References Cited

U.S. PATENT DOCUMENTS

| | | | | |
|---|---|---|---|---|
| 5,051,653 A | * | 9/1991 | DeBoer et al. | 313/489 |
| 5,635,249 A | * | 6/1997 | Haluska et al. | 427/387 |
| 5,717,282 A | | 2/1998 | Oomen et al. | 313/479 |
| 5,731,658 A | | 3/1998 | Lengyel et al. | 313/486 |
| 5,744,233 A | * | 4/1998 | Opitz et al. | 428/328 |
| 6,312,782 B1 | * | 11/2001 | Goldberg et al. | 428/67 |
| 6,677,407 B1 | * | 1/2004 | Bilgrien et al. | 525/478 |

FOREIGN PATENT DOCUMENTS

| | | |
|---|---|---|
| EP | 0 518 718 | 12/1992 |
| EP | 0 853 112 | 1/1998 |
| JP | 404174952 A * | 6/1992 |
| JP | 404174953 A * | 6/1992 |

OTHER PUBLICATIONS

Webb, C.; M. Dyson et al., Lasers in Surgery and Medicine, 22(5), S. 294–30 (1998).
Smol'yaninova, N.K., T.I.Karu et al., Biomedical Science, 2(2), S. 121–126 (1991).
Yaakobi, T., L. Maltz et al., Calcified Tissue International 59(4), S. 297–300 (1996).
Giavelli, S., Fava et al., Radiologia Medica, 95(4), S. 303–309 (1998).
Yu, H.S., K.L. Chang et al.,. Journal of Investigative Dermatology 107(4), S. 593–596 (1996).
Wilden, L and R. Karthein, Journal of Clinical Laser Medicine and Surgery 16(3), S. 159–165 (1998).
Patent Abstracts of Japn 09026511.

* cited by examiner

Primary Examiner—Ashok Patel
(74) Attorney, Agent, or Firm—Cohen, Pontani, Lieberman & Pavane

(57) ABSTRACT

A fluorescent film for use with a low-pressure discharge lamp is formed as a silicone elastomer in which luminescent particles are embedded. The film is formed by the steps of (a) mixing a hydroxyl polydiorganosiloxane with an organohydrogen siloxane, (b) adding luminescent particles, and (c) generating a chemical reaction by means of a platinum catalyst at room temperature.

24 Claims, 7 Drawing Sheets

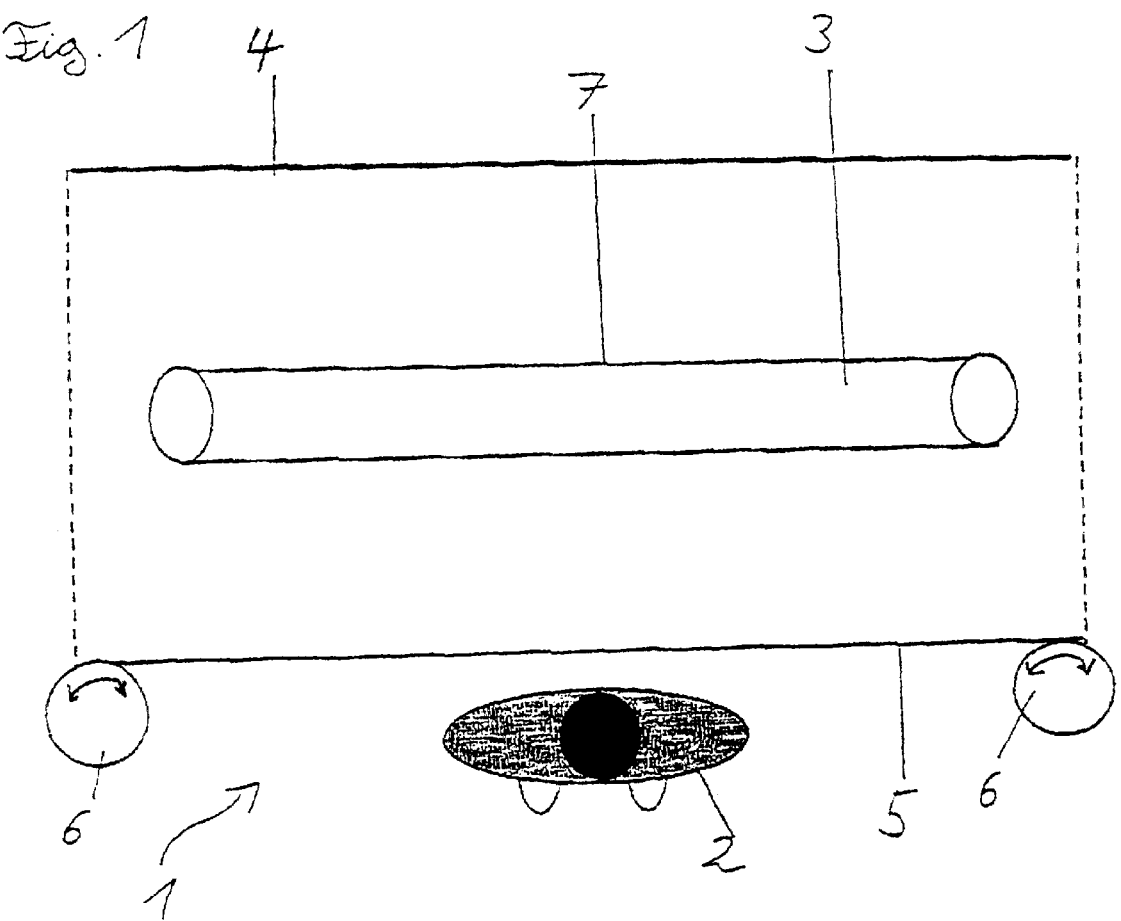

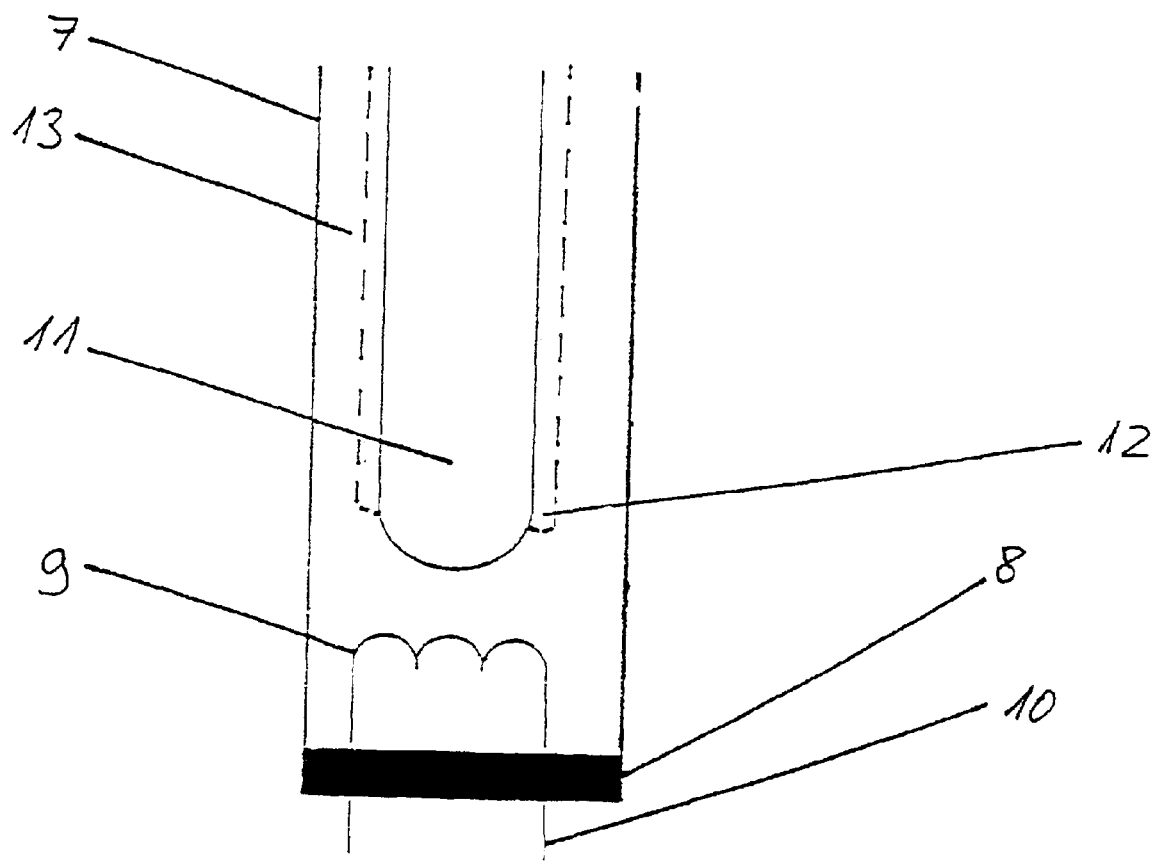

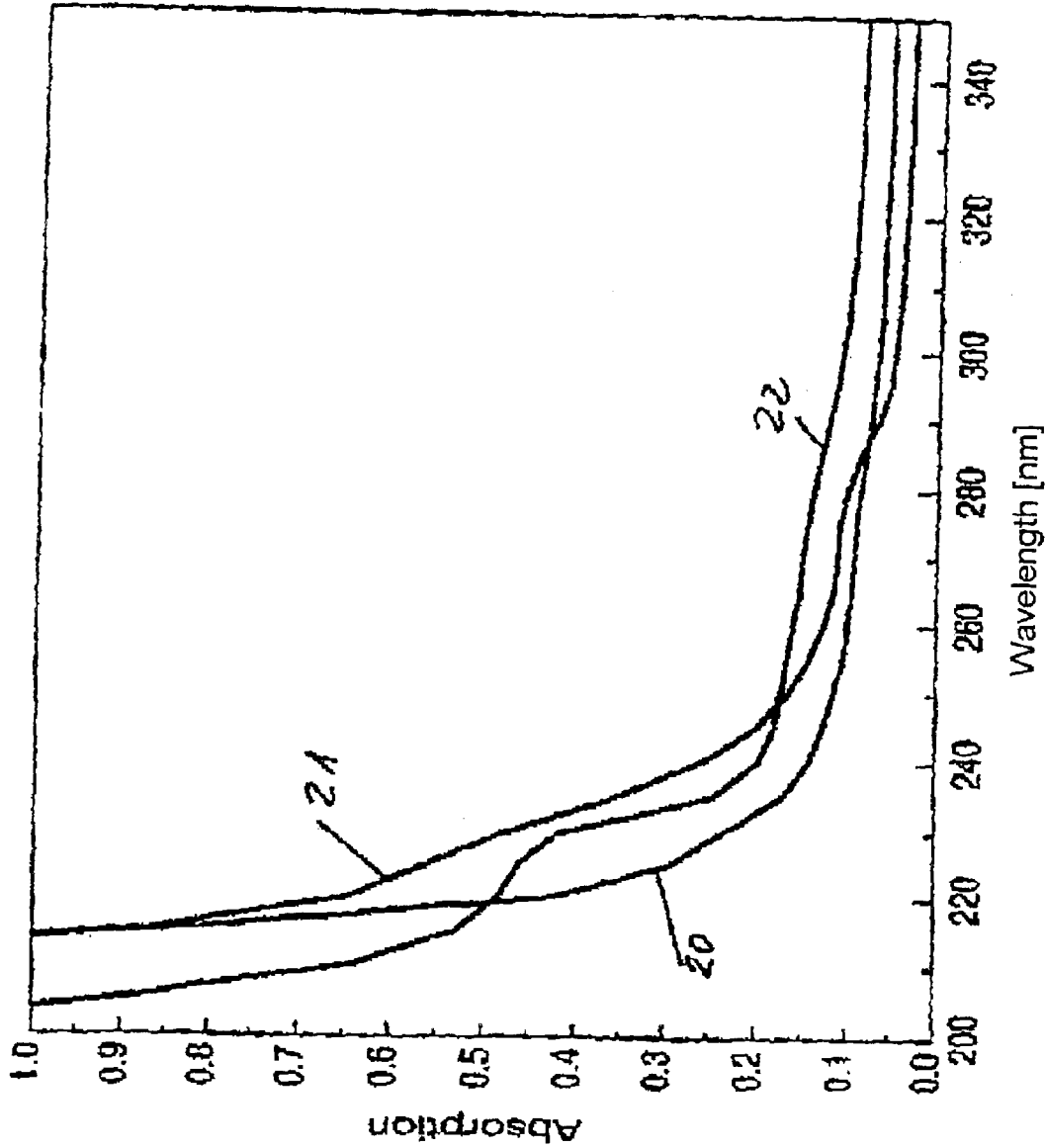

FLUORESCENT FILM WITH LUMINESCENT PARTICLES

This is a U.S. national stage of application No. PCT/DE00/03155, filed on 07 Sep. 2000. Priority under 35 U.S.C. §119(a) and 35 U.S.C. §365(b) is claimed from German Application No. 199 46 125.2, filed 20 Sep. 1999.

BACKGROUND OF THE INVENTION

1. Field of the Invention

The invention is directed to a fluorescent foil or film, particularly for use with a low-pressure discharge lamp, a method for producing the fluorescent film and an irradiation arrangement with the fluorescent film.

2. Description of the Related Art

Light absorption through the skin causes tissue changes by influencing the neuronal, lymphatic, vascular and immune systems. This brings about analgesic, antiinflammatory, antiedematous effects and stimulates healing of wounds. A considerable increase in fibroblasts of scar tissue was found under irradiation by red light (660 nm, 2.4–4 $J/cm^2$) (C. Webb; M. Dyson, et al., Lasers in Surgery and Medicine, 22(5), 294–30, (1998)). When peripheral lymphocytes were irradiated by an He-Ne laser with irradiation doses of between 28 and 112 $J/m^2$, there was an increase in RNA synthesis after stimulation of the lymphocytes by cytohemoagglutinin (N. K. Smol'yaninova, T. I. Karu, et al., Biomedical Science, 2(2), 121–126 (1991)). With bone injuries, a doubling of calcium incorporation at the injury site was observed after He—Ne laser irradiation (T. Yaacoby, L. Maltz, et al., Calcified Tissue International 59(4), 297–300, (1996)). Various chronic joint diseases such as gonarthrosis, LWS arthrosis and algodystrophy in hemiplegic stroke patients were found to be positively affected by He-Ne laser irradiation in over 400 patients (S. Giavelli, G. Fava, et al., Radiologia Medica, 95(4), 303–309, (1998)). The release of interleukin-1-alpha and interleukin-8 has been discussed as a possible cause for the positive effects (H. S. Yu, K. L. Chang, et al., Journal of Investigative Dermatology, 107(4), 593–596, (1996)). Irradiation at 1.5 $J/cm^2$ resulted in a concentration-dependent simulation of interleukin- 1-alpha production and corresponding mRNA expression. Since these cytokines stimulate both mobility and proliferation of keratinocytes, it is likely that these mechanisms directly promote wound healing. Further, models of photonic cellular energy transfer in relation to the respiratory chain are being discussed (L. Wilden, R. Karthein, Journal of Clinical Laser Medicine and Surgery, 16(3), 159–165, (1998). The biochemical models of cellular energy transfer take into account only the typical corpuscular aspect of electrons as responsible for energy transfer and ignore the wave-particle dualism of electrons in energy transfer. The light of the red and near-infrared spectra closely corresponds to characteristic energy planes and absorption rates of important components of the respiratory chain. For example, an increase in mitochondrial adenosine triphosphate production is brought about in this way. Interactions in the red and near-IR ranges can be explained on the basis of this interaction.

Photobiological effects in the non-UV range based on an interaction between endogenic or exogenic chromophores in the skin are becoming increasingly important because therapeutic effects can be influenced by means of suitable radiation sources in certain inflammatory skin diseases and, for example, impairment of wound healing in diabetes mellitus.

Because their efficiency is usually better than that of high-pressure lamps or temperature radiators, low-pressure discharge lamps are used increasingly in many technical fields, especially when high light energy efficiency is required. Single-base or double-base low-pressure discharge lamps are known depending on the field of use. Further, these low-pressure discharge lamps can be constructed with or without luminescent material and with different gases. However, all embodiment forms have in common that the light energy transfer increases as the diameter of the enveloping body decreases.

According to one model calculation, the light energy density corresponds to approximately one fourth of the quotient of the column capacity and projection surface. This means that the theoretical maximum value of a 38-mm low-pressure discharge lamp is approximately 45 $mW/cm^2$. In a 26-mm low-pressure discharge lamp, the light energy density increases to approximately 50 $mW/cm^2$. Theoretical light energy densities of 100, 125 and 170 $mW/cm^2$ result for lamp diameters of 16 mm, 12 mm and 8 mm. The increased luminous density of small radiators is utilized, for example, in the construction of compact lamps having, e.g., a wall diameter of 12 mm. Fluorescent tubes with a diameter of 8 mm have been in use for some years for effect illumination. They surpass compact lamps with respect to luminous density, but the greatest available lengths are only about 30 cm.

In spite of the increased light output, however, the reduction in lamp geometry has grave disadvantages. A large number of lamps with an equally large number of expensive ballast devices are required in order to generate radiating surfaces. The lengthening of the lamps is subject to plasma-physical limits because the high ignition voltages that are required for large lengths represent a considerable expenditure. Added to this is the manufacturing cost itself, i.e., elutriation, pumping and basing of each individual fluorescent tube.

Therefore, low-pressure discharge lamps with external or internal reflectors are usually used for surface illumination; for example, light energy densities of between 22 and 28 $mW/cm^2$ at an irradiation level of 100 W can be achieved. However, the light energy densities that can actually be achieved are considerably lower than in theory.

The basic problem in conventional low-pressure discharge lamps with fluorescent material and electron-emitting electrodes is the limited period of use, especially with very high lamp outputs.

The principal reason for this is that reaction components of the electrode burnup react chemically with the luminescent coating, which leads to an aging process. Another problem is that the reaction components of the electrode burnup and of the mercury vapor react with alkaline compounds of the glass tube to form various amalgams. This results in blackening of the tube, accelerated reduction of light output and sometimes in a dramatic reduction in the useful life of the lamp. Since the useful life is already sharply limited due to the aging process of the luminescent coating, the use of expensive alkali-free fused silica glasses has so far been unprofitable. For medical high-power radiators, the useful life may only amount to 48 hours, for example.

Experimental application of luminescent material to the outside of the low-pressure discharge lamp was not successful because the application of luminescent material in a non-inert atmosphere leads to a photochemical oxidative degradation of the hygroscopic luminescent material.

U.S. Pat. No. 5,717,282 discloses a Braun tube for monitor production in which a silica-containing paint with luminescent materials which is produced by a sol-gel process is applied to the outer side of the monitor. The thickness of this phosphor coating is limited to about 0.5 μm because, otherwise, cracks would result from the extensive shrinkage of the inorganic network. However, a layer of this thickness is too thin and does not have sufficient thermal stability for use in a low-pressure discharge lamp at higher outputs.

U.S. Pat. No. 5,731,658 discloses a liquid crystal display in which a phosphor coating is applied to the inner boundary walls. The phosphor coating comprises a UV-transparent carrier material and phosphor. Silicone oxide or organosilicates, particularly ethyl silicate, methyl silicate or isopropyl silicate, are suggested as carrier materials. The coating thickness that can be achieved in this way is also too small to allow for adequate embedding of luminescent material for a low-pressure discharge lamp.

SUMMARY OF THE INVENTION

Therefore, the object of the invention is to provide a fluorescent film which can be produced in sufficient thickness while exhibiting good thermal stability, so that it is suitable for use in low-pressure discharge lamps. Another object is to provide a flexible irradiation arrangement which can be used for a wide variety of applications. Another object is to provide a method for producing a fluorescent film of this kind.

According to the invention, the fluorescent film is formed as a silicone elastomer in which luminescent particles are embedded. The film is produced by the steps of (a) mixing a hydroxyl polydiorganosiloxane with an organohydrogen siloxane, (b) adding luminescent particles, and (c) generating a chemical reaction by means of a platinum catalyst at room temperature.

On one hand, films of sufficient thickness with a sufficiently high concentration of luminescent material can be produced in that the fluorescent film is formed as silicone elastomer in which the luminescent particles are embedded. Further, the luminescent particles are crosslinked so as to be airtight and free of moisture in the silicone elastomer, so that they are not subjected to an aging process. Silicone elastomers are UVC-transparent and have considerable advantages over alternative UVC-transparent carrier materials. While sapphire and quartz are transparent to UVC, it is not possible to use inorganic luminescent materials as a dopant in quartz windows for reasons pertaining to the chemistry of luminescent material. Sapphire dopant is ruled out from the start because of the extreme melting temperatures. Other plastics such as acrylates, transparent PVC or Teflon do not have sufficient thermal stability. However, the silicone elastomers are stable up to 250° C. and do not require emollients or other volatile substances that could evaporate. Because of the extended life of the luminescent material due to the fact that luminescent material can be arranged outside of the charging vessel and, therefore, no reaction can occur with the electrode burnup, the use of alkali-free fused silica is also acceptable, which further increases the life and quality of the low-pressure discharge lamp.

In a preferred embodiment form, the silicone elastomer can be produced by a method in which a hydroxyl polydiorganosiloxane with an organohydrogen siloxane to which the luminescent material particles are added is in crystalline form. By means of a platinum catalyst, a chemical reaction can be generated at room temperature leading to a complete crosslinking in which the luminescent material particles are not loaded due to the low process temperatures.

Hydroxyl polydiorganosiloxane comprising various polymers with a minimum viscosity of 1000 centipoise at room temperature has proven particularly suitable, wherein the hydroxyl diorganosiloxane is preferably formed as hydroxyl polydimethylsiloxane, its copolymers, phenylmethylsiloxane and/or polymethyl-3,3,3-trifluoropropylsiloxane.

The organohydrogen siloxane is preferably formed as silicone with at least 2 silicon-bonded hydrogen atoms per molecule, particularly homopolymers, copolymers or mixtures thereof.

The platinum catalyst can comprise a platinum salt, particularly platinum chloride or chloroplatinic acid, the latter preferably being used as a hexahydrate or in anhydrous form.

The thickness of the fluorescent film is preferably between 10 and 800 μm, wherein the surface density is between 1 and 20 mg/cm². A thickness between 100 and 600 μm with a surface density between 3 and 6 mg/cm² appears particularly advantageous.

An irradiation arrangement with very flexible handling can be constructed by arranging the fluorescent film outside the discharge space. For one, the life of the irradiation arrangement depends only upon the low-pressure discharge lamp itself, particularly its electrodes, since the fluorescent films themselves can easily be exchanged at any time. Further, this enables outfitting with differently doped fluorescent films in a very simple manner, so that different spectral ranges and irradiation intensities can be adjusted with one irradiation arrangement.

In a preferred embodiment form, a displacement body is arranged in the enveloping body, so that channels are formed between the enveloping body and displacement body, so that the low-pressure discharge lamp can be constructed so as to be very long without requiring very high ignition voltages, since there is still a sufficiently large plasma volume. On the other hand, the emitted light energy density increases in the channels between the enveloping body and the displacement cylinder because the channel acts like a low-pressure discharge lamp with a small diameter. When the enveloping body and displacement body are constructed as cylinders, a cylindrical jacket is formed as a channel which can be visualized as many low-pressure discharge lamps of small diameter arranged radially with respect to one another.

In a preferred embodiment form, the displacement body is constructed as a closed hollow body which is particularly advantageous with respect to weight.

A reflector layer can also be arranged on the outer side of the displacement body or the displacement body can comprise a material which is transparent to the emitted radiation. Further, it is also possible to combine the steps.

In order to produce low-pressure discharge lamps with different light energy densities, a fastening device can be used to receive different displacement bodies. For production, different diameters of the displacement body are used depending on the desired light energy density.

In certain applications, it is desirable to obtain uniform light energy density over the entire irradiation surface. For sunbathing, for example, a stronger radiation may be desired only in the head area. This can easily be achieved, for example, in that the displacement body only extends over the head area or in that the displacement body has different diameters in longitudinal direction. A further possibility consists in coating the displacement body with a reflector layer at desired places.

The possibility of operating different screen-like irradiation films with different luminescent materials with one and the same light source results in a very multifaceted therapeutic and irradiation system. The treating physician can treat a different patient or replace an old silicone module in a very short amount of time, i.e., in a minute, by changing the silicone module similar to the use of a large optical filter.

The invention will be described more fully in the following with reference to a preferred embodiment example.

BRIEF OF THE DRAWINGS

FIG. 1 shows a schematic top view of an irradiation arrangement;

FIG. 2 shows a schematic partial top view of a low-pressure discharge lamp;

FIG. 6 shows spectral absorption curves of a fluorescent film with variation in time.

DETAILED DESCRIPTION OF THE PRESENTLY PREFERRED EMBODIMENTS

Figure 2A:
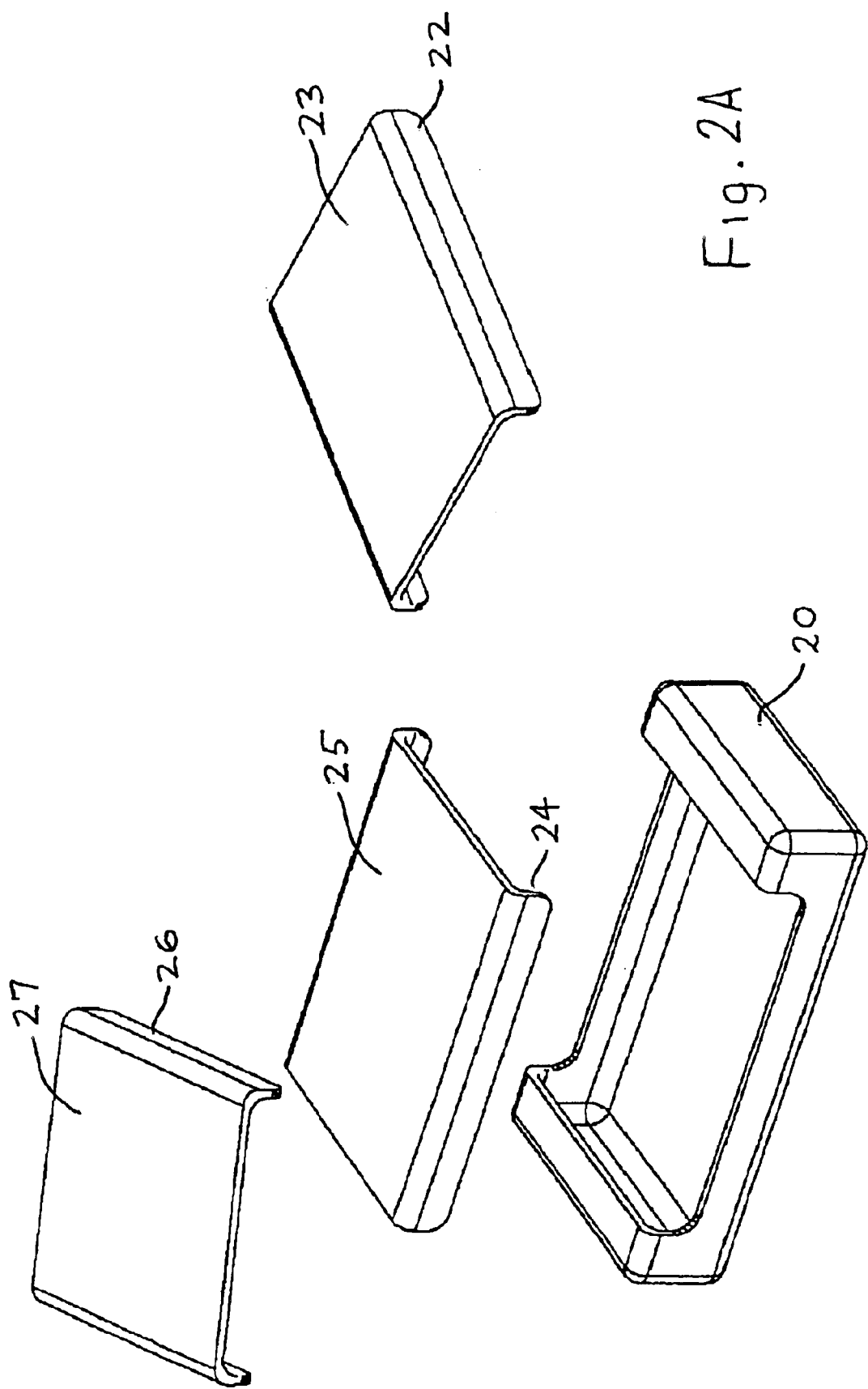
FIG. 2A shows an enclosure having interchangeable covers carrying a fluorescent film.

FIG. 1 shows a schematic top view of an irradiation arrangement 1 for cosmetic and/or therapeutic treatment of a patient 2. The irradiation arrangement 1 comprises at least one low-pressure discharge lamp 3, a reflector screen 4 and a fluorescent film 5 which is supported so that it can be wound on and off by means of rollers 6. The distances shown between the low-pressure discharge lamp 3 and the reflector screen 4 and fluorescent film 5 are not true to scale. The UV radiation generated in the discharge program of the low-pressure discharge lamp 3 exits isotropically from the UV-transparent enveloping tube 7 of the low-pressure discharge lamp 3 and impinges in part directly on the fluorescent film 5. Another portion of the radiation impinges on the reflector layer 4 and is partially reflected from the latter to the fluorescent film 5. The UV radiation impinging on the fluorescent film 5 partially excites the luminescent particles embedded in the fluorescent film 5 which then emit in the desired spectral range and irradiate the patient. Various types of irradiation arrangements 1 can be realized by means of the rollers 6 onto which a portion of the fluorescent film 5 is wound.

In the simplest case, the rollers 6 extend over the full height of the irradiation arrangement 1 on which a uniformly doped fluorescent film 5 is wound. Then, in case the luminescent material located in the wound-off area should be aged, this area is wound up and an unused portion of fluorescent film 5 is wound off. Further, it is also possible to use fluorescent films 5 with different doping, so that a determined region of the fluorescent film 5 with the appropriate doping depending on the desired irradiation therapy is wound off. Further, it is possible to provide different rollers 6 along the height, so that the variation described above can also be carried out for different body parts.

FIG. 2 shows a preferred embodiment form of a low-pressure discharge lamp 3 in a schematic partial top view. The low-pressure discharge lamp 3 comprises an enveloping body 7, a base 8 hermetically closing the enveloping body 7, an incandescent spiral filament 9 with contacts 10 guided through the base 8 and a displacement body 11 constructed as a hollow body. The displacement body 11 is arranged so as to be rotationally symmetric with respect to the enveloping body 7 and at a distance from the spiral filament 9. A reflecting coating 12 is arranged on the outer side of the displacement body 11. A rotationally symmetric channel 13 with the low-pressure plasma is formed between the enveloping body 7 and the displacement body 11, wherein mercury with argon is preferably used as filling material. Electrons are emitted via the spiral filament 9 by thermal emission and are accelerated by an external electrical field. This brings about an interaction with the mercury atoms in the channel 13. The electrons of the mercury are excited by the interaction and give off the absorbed energy again by means of spontaneous emission of photons. The resulting UV radiation then exits the enveloping body 7 directly or after being reflected at the coating 12 and excites the luminescent particles in the fluorescent film arranged outside the low-pressure discharge lamp 3.

Figure 3:
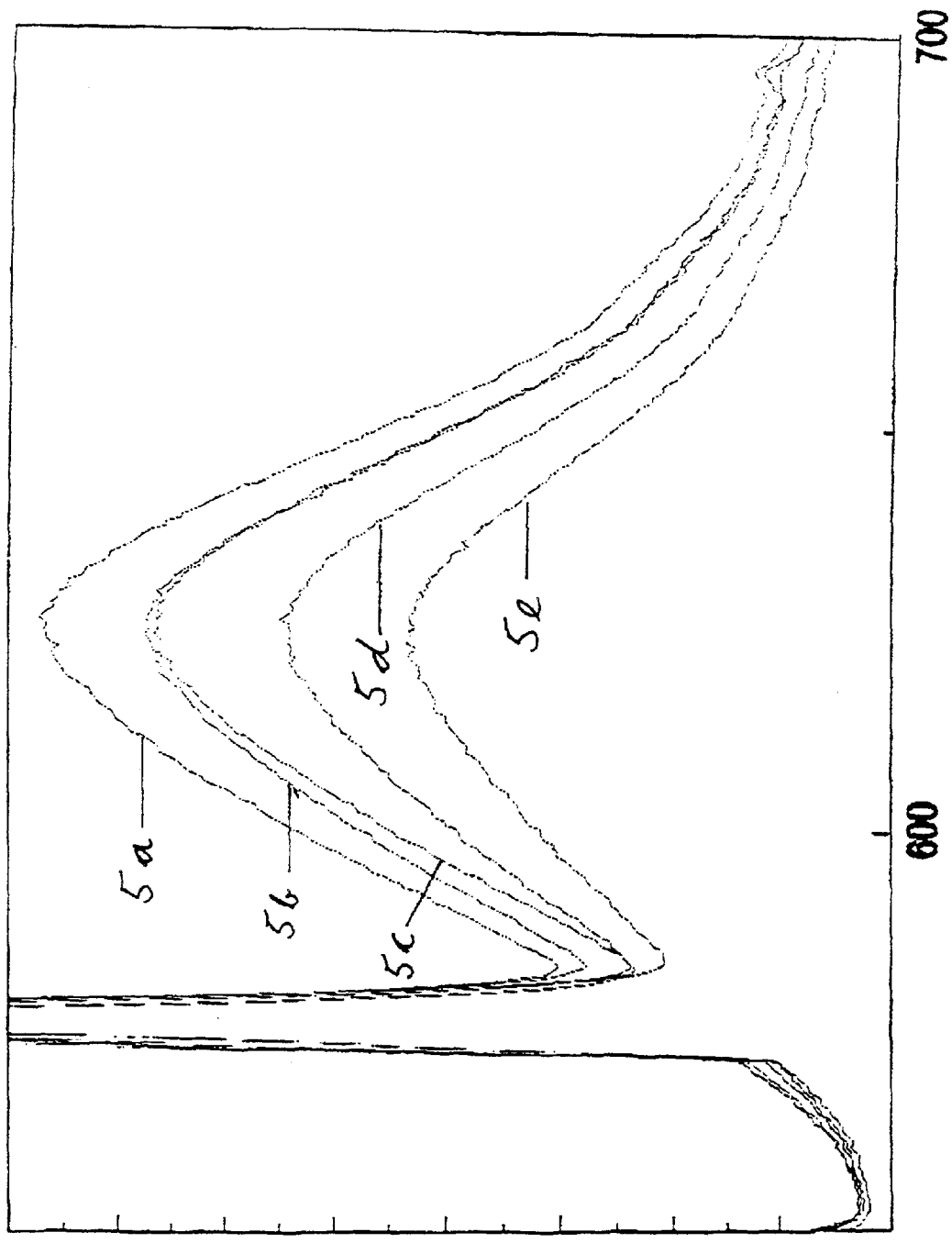
FIG. 3 shows spectra of different fluorescent films.

FIG. 2A shows an enclosure for the discharge lamp, which includes a frame 20 having interchangeable covers 22, 24, 26, each cover having a respective fluorescent film 23, 25, 27 with particles which are excited by radiation from the lamp. FIG. 3 shows the intensities of different fluorescent films with different film thickness and different dopant concentrations for a luminescent material LS 635. The fluorescent films 5a–e have the following parameters:

| Film | Film thickness (mm) | Doping (g/cm$^3$) | Surface density of the luminescent material particles (mg/cm$^3$) |
|---|---|---|---|
| 5a | 0.2 | 0.2 | 4 |
| 5b | 0.55 | 0.1 | 5.5 |
| 5c | 0.6 | 0.2 | 12 |
| 5d | 0.25 | 0.5 | 12.5 |
| 5e | 0.65 | 0.3 | 19.5 |

Figure 4:
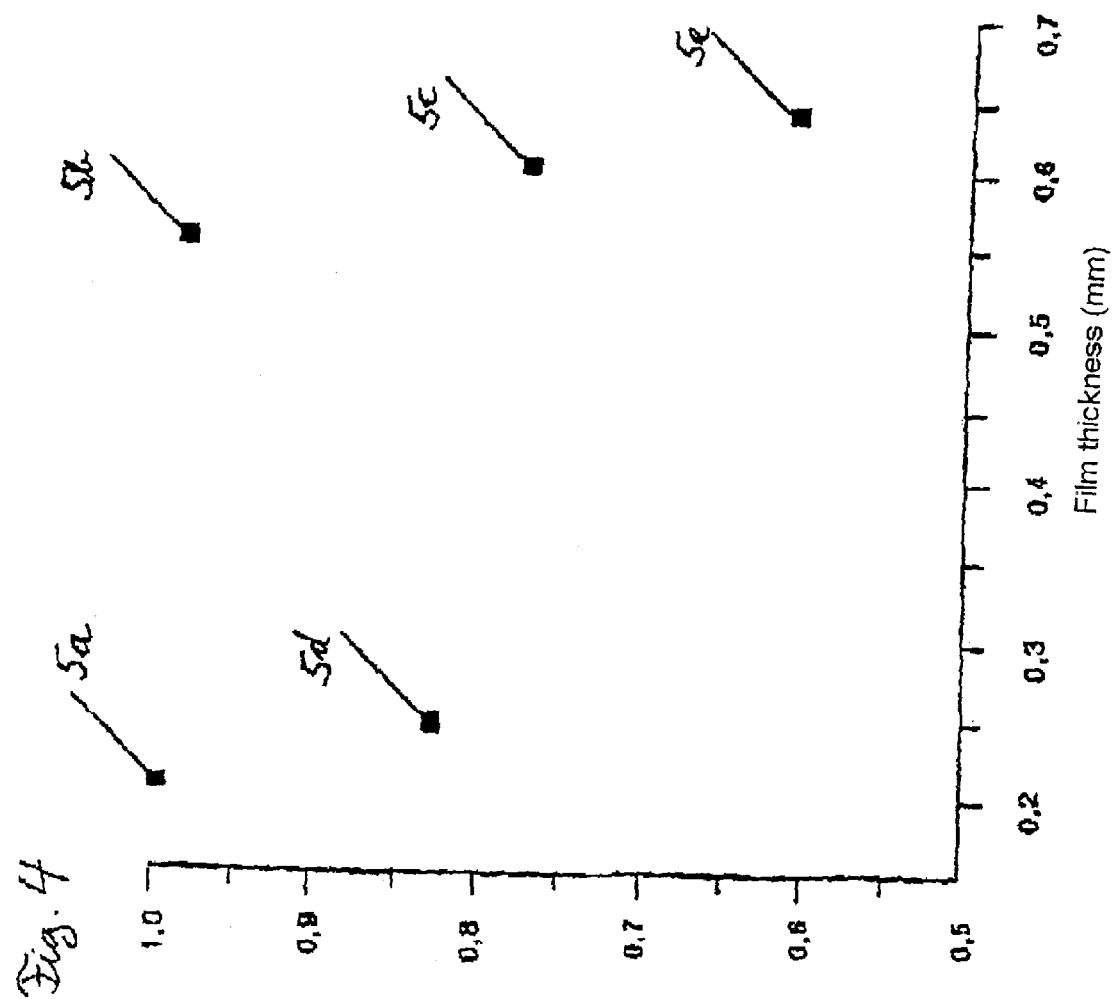
FIG. 4 is a graph showing intensities over film thickness.
Figure 5:
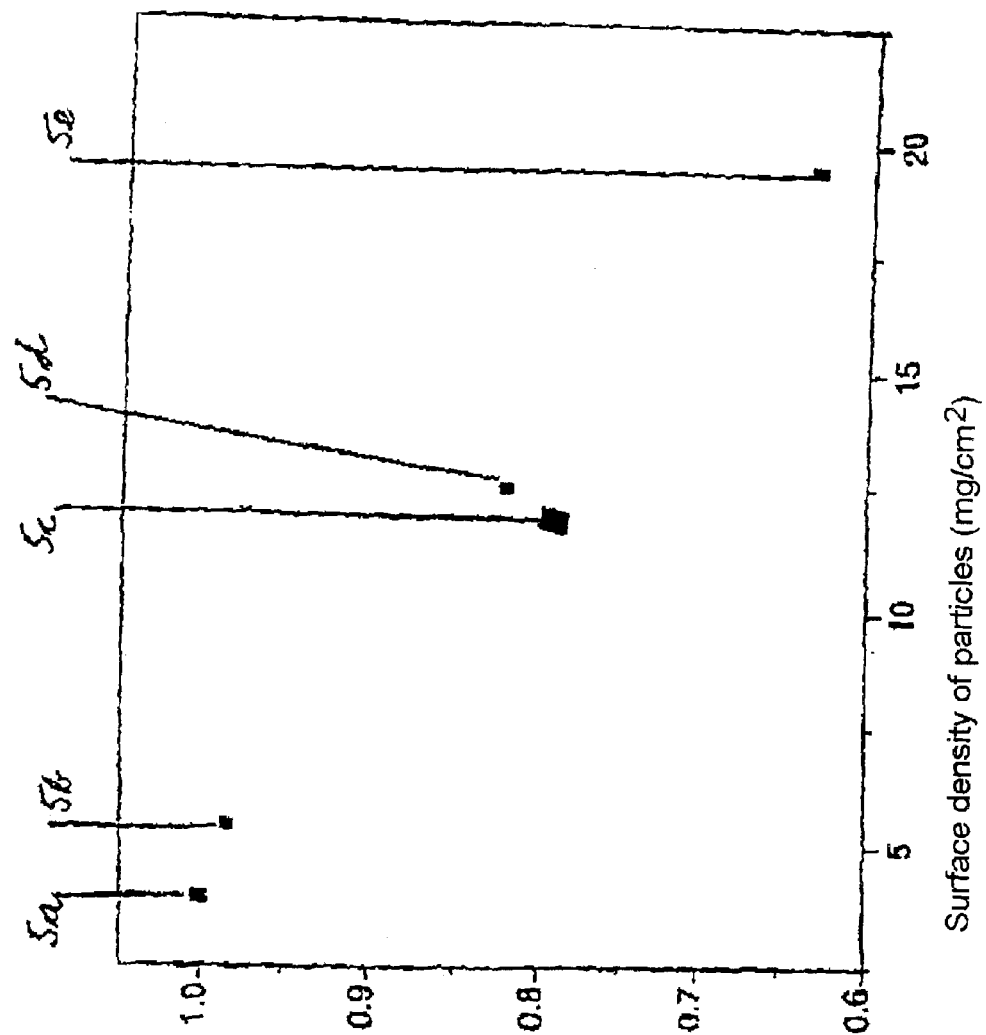
FIG. 5 is a graph showing intensities over the surface density of the luminescent particles.

FIGS. 4 and 5 show the fluorescent films 5a–e with a standardized intensity over the film thickness and surface density of the luminescent particles. As will be seen particularly from FIG. 5, there are high intensities in the range of 4–6 mg/cm$^2$ surface density of the luminescent particles. Further, it will be seen, referring to fluorescent film 5e, for example, that especially thick films with high doping do not lead to high intensities, which is presumably to be credited to the vignetting effect and self-excitation. The present measurements lead to the conclusion that an optimum exists with respect to film thickness and surface density, presumably dependent on the luminescent material, which must presumably be empirically determined. However, it is obvious from FIG. 5 that the essential parameter is the surface density of the luminescent particles because films 5a and 5b; 5c and 5d behave virtually identically in spite of considerable differences in thickness.

Therefore, in principle, thin films appear more suitable because they require considerably less material for the same intensity, but their temperature stability and life compared with thicker films must be studied in greater depth.

FIG. 6 shows the spectral UV absorption curve 20 of a fluorescent film with a thickness of 530 $\mu$m. Further, the UV absorption curve 21 of this film after 5 days continuous loading by a 54 W UV lamp at a distance of 2 cm is 60° C. and the UV absorption curve 22 after 7 days of continuous loading by a 54 W UV lamp is 60° C., where the film lay directly on the enveloping tube. These curves are an impressive demonstration of the long life of the film, whose absorption curve also remains virtually unchanged even with continuous loading.

What is claimed is:

1. A fluorescent film formed as a silicone elastomer in which hydroxyl polydiorganosiloxane and organohydrogen siloxane are cross-linked and in which luminescent particles are embedded.

2. A fluorescent film according to claim 1, wherein the hydroxyl polydiorganosiloxane comprises various polymers with a minimum viscosity of 1000 centipoise at 25° C.

3. A fluorescent film according to claim 2, wherein the hydroxyl polydiorganosiloxane is formed as at least one of hydroxyl polydimethylsiloxane, its copolymers, phenylmethylsiloxane and polymethyl-3,3,3-trifluoropropylsiloxane.

4. A fluorescent film according to claim 2 wherein the organohydrogen siloxane is formed as silicone with at least two silicon-bonded hydrogen atoms per molecule.

5. A fluorescent film according to claim 4 wherein the organohydrogen siloxane comprises one of homopolymers, copolymers, and mixtures thereof.

6. A fluorescent film according to claim 1 wherein the fluorescent film has a thickness between 10 and 800 $\mu$m.

7. A fluorescent film as in claim 1 wherein the luminescent particles have a surface density which is between 1 and 20 $mg/cm^2$.

8. A fluorescent film according to claim 1 wherein the luminescent particles have a grain size which is between 5 and 15 $\mu$m.

9. An irradiation arrangement comprising:
   a low-pressure discharge lamp with an enveloping body which is transparent to UVC, and electrodes which can be contacted from the outside projecting into the enveloping body, and
   a fluorescent film formed as a silicone in which elastomer hydroxyl polydiorganosiloxane and organohydrogen siloxane are cross-linked and in which luminescent particles are embedded.

10. An irradiation arrangement according to claim 9, wherein the fluorescent film is applied to an outer surface of the enveloping body.

11. An irradiation arrangement according to claim 10 wherein fluorescent films with different doping are applied to the enveloping body.

12. An irradiation arrangement according to claim 9 further comprising a displacement body arranged in the enveloping body, so that channels are formed between the enveloping body and displacement body.

13. An irradiation arrangement according to claim 12, wherein the displacement body is constructed as a closed hollow body.

14. An irradiation arrangement according to claim 12 further comprising a reflector layer applied to an outer surface of the displacement body.

15. An irradiation arrangement according to claim 12 wherein the displacement body comprises a material that is transparent to radiation emitted by the discharge lamp.

16. An irradiation arrangement according to claim 9 wherein the fluorescent film is fitted to the enveloping body in the form of an interchangeable frame.

17. An irradiation arrangement according to claim 9, further comprising a dispensing roller and a take-up roller on which the fluorescent film is wound up, whereby films with different doping can befitted to the enveloping body.

18. A method for producing a fluorescent film formed as a silicone elastomer in which luminescent particles are embedded, comprising the following steps:
   (a) mixing a hydroxyl polydiorganosiloxane with an organohydrogen siloxane,
   (b) adding luminescent particles, and
   (c) generating a chemical reaction by means of a platinum catalyst at room temperature.

19. A method for producing a fluorescent film according to claim 18, wherein the hydroxyl polydiorganosiloxane comprises various polymers with a minimum viscosity of 1000 centipoise at 25° C.

20. A method for producing a fluorescent film according to claim 19, wherein the hydroxyl polydiorganosiloxane is formed as at least one of hydroxyl polydimethylsiloxane, its copolymers, phenylmethylsiloxane, and polymethyl-3,3,3-trifluoropropylsiloxane.

21. A method for producing a fluorescent film according to claim 18 wherein the organohydrogen siloxane is formed as silicone with at least two silicon-bonded hydrogen atoms per molecule.

22. A method for producing a fluorescent film according to claim 21 wherein the organohydrogen siloxane comprises one of homopolymers, copolymers, and mixtures thereof.

23. A method for producing a fluorescent film according to claim 18 wherein the platinum catalyst comprises one of a platinum chloride, platinum salts, and chloroplatinic acid.

24. A method for producing a fluorescent film according to claim 23, wherein the chloroplatinic acid is in the form one of a hexahydrate and anhydrous chloroplatinic acid.

* * * * *